United States Patent [19]

Kaiser

[11] 4,289,710

[45] Sep. 15, 1981

[54] PROCESS FOR PRODUCING METHANOL FROM SYNTHESIS GAS WITH PALLADIUM-CALCIUM CATALYSTS

[75] Inventor: Steven W. Kaiser, South Charleston, W. Va.

[73] Assignee: Union Carbide Corporation, New York, N.Y.

[21] Appl. No.: 105,408

[22] Filed: Dec. 19, 1979

[51] Int. Cl.$^3$ .................... C07C 27/06; C07C 31/04
[52] U.S. Cl. ................................ 518/717; 252/457; 252/460; 252/466 PT; 252/447
[58] Field of Search ................................ 260/449.5

[56] References Cited

U.S. PATENT DOCUMENTS 1,681,753  8/1928  Storch .............................. 260/449.5
4,119,656 10/1978  Poutsma et al. ............... 260/449.54

Primary Examiner—Howard T. Mars
Attorney, Agent, or Firm—Bernard Lieberman

[57] ABSTRACT

An improved catalytic process for the production of methanol from hydrogen and carbon monoxide at a temperature of from about 200° C. to about 400° C. and a pressure of from about 150 to about 20,000 psia which comprises effecting the reaction in the presence of a heterogeneous solid catalyst comprising palladium and calcium.

6 Claims, No Drawings

4,289,710

PROCESS FOR PRODUCING METHANOL FROM SYNTHESIS GAS WITH PALLADIUM-CALCIUM CATALYSTS

CROSS REFERENCE TO RELATED APPLICATION

This application is related to copending U.S. application Ser. No. 105,407 filed on even date herewith which describes a process for producing methanol from synthesis gas using a catalyst containing palladium in combination with a metal additive selected from the group consisting of lithium, magnesium, strontium, barium, molybdenum and mixtures of the same.

BACKGROUND OF THE INVENTION

This invention relates, in general to a process for producing methanol from synthesis gas. More particularly, the invention concerns reacting synthesis gas in the presence of a catalyst containing palladium and calcium under suitable reaction conditions to form methanol at high carbon efficiencies and improved rates of production.

Methanol is an increasingly important feedstock for the production of carbon-based chemicals. Existing or proposed commercial processes using methanol include dehydrogenation to form formaldehyde, carbonylation to form acetic acid, homologation to form ethanol and reactions over zeolitic materials to form gasoline-grade fractions. The presently anticipated increase in commercial methanol manufacture has underscored the need for new and improved catalysts characterized by high carbon efficiencies and good productivity to methanol.

The use of catalysts to influence the product distribution resulting from the hydrogenation of carbon monoxide is well known in the art. Among the vast array of products obtainable from the reaction of carbon monoxide and hydrogen, methane is thermodynamically the most favored, longer chain hydrocarbons are next followed by high molecular weight alcohols with methanol being thermodynamically one of the least stable products which can be formed. Hence, specific catalysts for methanol synthesis are required in order to selectively produce methanol at high reaction efficiencies from synthesis gas. The prevalent commercial catalysts today for methanol manufacture from a synthesis gas are composed of oxides and mixed oxides of chromium, zinc and copper.

Palladium is also known in the art as an effective methanol catalyst. U.S. Pat. No. 4,119,656 to Poutsma et al., dated Oct. 10, 1978, discloses the formation of hydroxylated hydrocarbons such as methanol and ethylene glycol from synthesis gas in the presence of a palladium catalyst. While the process of Poutsma et al is characterized by very high selectivities to methanol, generally about 95 percent, the productivity of methanol is substantially below that achieved in commercial methanol synthesis processes. Hence, it would be desirable to significantly improve the methanol production rate of the Poutsma et al process while maintaining its high process efficiency.

Palladium catalysts supported on carriers containing calcium, among other materials, are disclosed in the Poutsma et al patent. Specifically, Table I of U.S. Pat. No. 4,119,656 describes the various palladium catalysts which were experimentally used to produce methanol and other hydroxylated hydrocarbons, all of which catalysts were supported on Davison ™ Grade 57 silica. At column 4, line 40 of the patent, the chemical analysis of such silica is provided and shown to contain 0.03% CaO (corresponding to 0.021% Ca). Hence, the use of palladium catalysts containing 0.021% Ca for methanol manufacture from synthesis gas has been reported in the prior art.

SUMMARY OF THE INVENTION

The invention describes a catalyst for the production of methanol from the reaction of carbon monoxide and hydrogen, such catalyst being an improvement of that disclosed in the aforementioned U.S. Pat. No. 4,119,656. The process of the invention involves contacting a heterogeneous solid catalyst comprising palladium and calcium with a synthesis gas comprising carbon monoxide and hydrogen at suitable reaction conditions to selectively form methanol, the concentration of calcium in the catalyst being at least 0.03 weight percent based on the weight of the catalyst and support.

The reaction conditions include a temperature of from about 200° C. to about 400° C. and a pressure of from about 150 to about 20,000 psia. The preferred reaction conditions are a temperature between about 250° C. and about 350° C. and a pressure between about 150 and about 3,000 psia.

The present invention is predicated on the discovery that the production rate of methanol in the aforementioned Poutsma et al process can be significantly enhanced by the addition of calcium to a palladium catalyst such as utilized in the Poutsma et al process. Thus, approximately a three-fold increase in methanol manufacture can be achieved in accordance with the invention relative to the process of U.S. Pat. No. 4,119,656 without adversely affecting the very high process efficiencies achieved with such process.

PROCESS DISCUSSION

In accordance with the invention, a synthesis gas containing carbon monoxide and hydrogen is contacted with a supported palladium catalyst containing at least 0.03 weight percent calcium under reaction conditions of temperature and pressure which thermodynamically favor the formation of methanol relative to hydrocarbons, such as methane. The selectivity of the reaction to methanol is generally at least 90 percent, more typically about 95 percent or greater, and under preferred reaction conditions about 98 percent.

Reaction selectivity, or efficiency, is defined herein as the percentage of carbon atoms converted from carbon monoxide to a specified compound other than $CO_2$.

The promoted palladium catalyst of the invention comprises palladium in combination with calcium employed in a fine dispersion or slurried in a high boiling point solvent, or alternatively, supported upon an inert carrier material. The preferred mode of operation is to deposit palladium and calcium onto a particulate high surface area support material and the supported combination then placed into the reaction zone. In an alternate embodiment of the invention, calcium is incorporated into the support during formulation so as to be an integral part of the finished support, the palladium being thereafter deposited on such support. If desired, a portion of the calcium may be incorporated into the support and the remainder deposited upon the support with the palladium catalyst.

A support having a surface area greater than 1.0 square meters per gram (BET low temperature nitrogen adsorption isotherm method) is generally preferred, a surface area above 10 square meters per gram being particularly desirable although surface area is not the sole determinative variable. Silica gel is a preferred catalyst support with alpha alumina, gamma alumina, magnesia, carbon, zirconia and titania being among the useful albeit less desirable catalyst supports.

For the purpose of this invention it is believed that palladium deposited on particles of a compound of calcium such as calcium oxide or calcium carbonate is substantially the same as palladium and calcium deposited on any of the above support materials.

On the basis of experience to date, the amount of palladium on the support should range from about 0.1 wt. % to about 20 wt. %, based on the weight of the support material. Preferably, the amount of palladium is within the range of about 2 to about 5 weight percent. The amount of calcium in the catalyst may vary depending upon the catalyst support employed and the method of catalyst preparation. The optimum concentration of calcium is readily determined by simple experimentation. Generally, the concentration of calcium is at least 0.03% and as high as 2.0% by weight of the catalyst support, the preferred concentration being from about 0.05 to about 1% by weight.

The palladium and calcium may be deposited onto the catalyst base or support by any of the commonly accepted techniques for catalyst preparation, as for example, impregnation from a solution containing the salts of palladium and calcium, precipitation, coprecipitation, or ion exchange. Typically, a solution of heat decomposable inorganic or organic palladium compound and a compound of calcium is contacted with the support material and then dried and heated, the latter under reducing conditions to form the finely dispersed promoted palladium catalyst.

The calcium promoter and palladium metal catalyst may be deposited concurrently or sequentially. That is, palladium may be codeposited with calcium or it may be deposited upon the carrier either before or after the deposition of calcium.

The palladium deposited is typically in metal form, desirably as fine discrete particles. The form of the calcium component is, however, not completely understood. It may be chemically associated with the palladium or it may be a physical admixture. For example, the calcium may be alloyed with the palladium or not, in the form of a metal or an oxidized of the metal, or it may be a silicate, carbonate, or the like.

Conditions of temperature, of pressure, and of gas composition are within the ranges that are essentially conventional for synthesis gas conversion to methanol for palladium catalysts. The reaction temperature markedly affects the productivity of the reaction with regard to methanol formation. Thus, an increase in reaction temperature results in an increased conversion to methanol with the proviso that the reaction pressure is correspondingly increased to avoid thermodynamic limitations. Increased pressure enhances the productivity of the reaction but may affect product distribution. Thus, for example, at increased pressures there may be an increased proportion of impurities, such as, ethanol and methyl formate in the product mixture. For purposes of economy, the reaction pressure is preferably within the range of 150-3,000 psia although a reaction pressure of from about 150-20,000 psia is generally suitable.

The operable space velocities in the flow reactor may vary from about $10^2$ to $10^6$ per hour; space velocity being defined as volumes of reactant gas at 0° C. and 760 mm. Generally, the higher the space velocity, the more economical the overall reaction, although at excessively high space velocities the productivity of the reaction is adversely affected while excessively low space velocities cause the production of a more diverse spectrum of reaction products.

The molar ratio of hydrogen to carbon monoxide in the synthesis gas may vary extensively from about 1:10 to 10:1. The preferred hydrogen to carbon monoxide ratio is within the range of at least 1:5 to 5:1; a ratio of about 2:1 being most preferred. Increasing the percentage of hydrogen relative to carbon monoxide in the gas mixture increases the rate of the reaction, but adversely affects the economics of the overall process.

PREPARATION OF CATALYSTS

The catalysts cited in the examples below were all prepared by essentially the following sequence of steps: The desired quantities of palladium (II) chloride, and calcium nitrate, depending upon the desired catalyst composition, were dissolved in a 1:1 $HCl/H_2O$ (by volume) solution at ambient temperature. The volume of solution was chosen to just fill the void volume (pores) of the support sample being impregnated. Davison TM Grade 59 silica gel (8-20 mesh—U.S. Sieves) was placed in a vacuum flask. The top of the flask was sealed with a rubber septum, and the flask was evacuated through the side arm. A syringe needle was then used to inject the solution onto the evacuated support. When addition was complete, the impregnated support was allowed to stand at one atmosphere for approximately 30 minutes. It was then carefully dried in a nitrogen atmosphere using the following sequence: 80° C. (for 1 hr.); 110° C. (2 hrs.); 150° C. (2 hrs.); and about 300° C. (2 hrs.). The dried, impregnated support was placed in a quartz tube through which hydrogen was continuously passed. The temperature was raised from 100° to 500° C. over a five hour period and then held at 500° C. for 1 hour. The reduced catalyst was then cooled to ambient temperature in a flowing hydrogen atmosphere and finally flushed with nitrogen before being removed.

In order to remove significant fractions of impurities which were present in the support material as received from the manufacturer, the Davison TM Grade 59 silica support was initially "washed" with oxalic acid prior to being used as the catalyst support. Such treatment consisted of passing a mixture of oxalic acid, glycerine, and water in proportions of 1:1.5:2.5 by weight, respectively, through a bed of support material (length/diameter ratio of about 20 to 25) contained within a glass tube which drained through a stopcock at its base. The contents of the tube were maintained at about 90° C. by means of resistance heating wire wrapped around the exterior of the tube. About 2.5 volumes of oxalic acid solution was used to wash one volume of 8-20 mesh silica gel over a three-hour period. The material was then washed with about six volumes of distilled water at 90° C. over a period of about four hours and then dried at 350° C. for about four hours.

The chemical analysis of the silica gel for iron, aluminum, sodium and calcium impurities following the above-described treatment was as follows:

| | |
|---|---|
| Iron as $Fe_2O_3$ | 0.01% ± 0.004% |
| Aluminum as $Al_2O_3$ | 0.01% ± 0.004% |
| Sodium as $Na_2O$ | 0.01% ± 0.004% |
| Calcium as $Ca_2O$ | 0.02% ± 0.01% |

DESCRIPTION OF TEST REACTOR

The reactor used in the following Examples was an internally silver-plated 316 stainless steel, bottom-agitated "Magnedrive" autoclave with a centrally positioned catalyst basket and a side product effluent line. It is of the type depicted in FIG. 1 of the paper by Berty, Hambrick, Malone and Ullock, entitled "Reactor for Vapor-Phase Catalytic Studies", presented as Preprint 42E at the Symposium on Advances in High-Pressure Technology—Part II, Sixty Fourth National Meeting of the American Institute of Chemical Engineers (AIChE), at New Orleans, Louisiana, on March 16-20, 1969 and obtainable from AIChe at 345 East 47th Street, New York, N.Y. 10017. A variable speed, magnetically driven fan continuously recirculated the reaction mixture over the catalyst bed. The following modifications were found to facilitate operation:

1. Hydrogen feed gas was introduced continuously at the bottom of the autoclave through the well for the shaft of the Magnedrive agitator.
2. Carbon monoxide feed gas was introduced continuously through a separate port at the bottom of the autoclave, in order to avoid a hydrogen-rich zone in the autoclave.

Effluent gases were removed through a port in the side of the reactor. Condensable liquid products were removed from the exit stream in a brine-cooled condenser at ca. 5° to 10° C. and were collected in a holding tank under pressure. The non-condensable components of the exit stream were vented through a wet test meter at atmospheric pressure to determine their total volume. A rubber spectrum in the atmospheric pressure line permitted syringe sampling of the non-condensable gases. No external recycle was employed.

DESCRIPTION OF THE TEST PROCEDURE

The weight of a given volume of catalyst sample was determined and the sample was placed in the catalyst basket. The quantity of catalyst charged was from about 25 to about 50 cc. depending upon the particular sample. Silver-plated screens and thin layers of glass wool were placed above and below the catalyst bed to prevent circulation of solid fines. The catalyst basket was charged to the reactor, and the reactor then sealed. The sealed reactor and the process lines were pressure tested at operating pressure. Nitrogen, hydrogen, or a mixture of the two was used for this test.

When the reactor was shown to be leak free, pure hydrogen was passed through the reactor, and the temperature raised to about 240° C. The hydrogen and carbon monoxide flows were then adjusted at the desired molar ratio to give a total pure rate of approximately 500 STP* liters/hr. This corresponds to a space velocity of from about 10,000 to about 20,000 STP volumes of gas per volume of catalyst per hour depending upon the volume of catalyst charged in the particular example. The hydrogen-carbon monoxide ratio was determined by gas chromatographic analysis of an effluent gas aliquot.

*"STP" means standard temperature and pressure defined as 0° C. and 1 atm. pressure.

When the appropriate gas composition was obtained, the reactor temperature was raised to 300° C. A period from about 0.5 hour to about one hour was allowed for the reactor to reach a steady-state at this temperature. The liquid product trap was then drained, a wet test meter reading was taken, and the time was noted at the beginning of a run. During the course of a run, one or more effluent gas samples were analyzed for hydrogen, carbon monoxide, methane, $C_2$ and $C_3$ hydrocarbons, methanol, ethanol, methyl formate, dimethyl ether and acetaldehyde. At the end of a run, the liquid product was collected, and the volume of effluent gas was noted. The liquid product was analyzed by gas chromatography.

The results of the tests are shown in Tables I and II. Examples B to E and G to J of Table I demonstrate the effect of calcium deposition with regard to the rate of methanol production of the catalyst. Examples A and F disclose catalysts containing no calcium other than that present in the catalyst support (approximately 0.02%), Examples A and F being provided for comparative purposes.

Examples K to N of Table II demonstrate the efficacy of the invention with alpha alumina and magnesium oxide catalyst support.

TABLE I
METHANOL PRODUCTION DATA[a] FOR SUPPORTED PALLADIUM CATALYSTS[b] CONTAINING VARYING AMOUNTS OF CALCIUM

| Example | Calcium Deposited[c] (weight percent) | Rate of Methanol[d] |
|---|---|---|
| | 70/30 $H_2$/CO Synthesis Gas Composition | |
| A | None | 16.3 |
| B | 0.1 | 34.6 |
| C | 0.2 | 43.6 |
| D | 0.5 | 42.2 |
| E | 1.0 | 32.8 |
| | 50/50 $H_2$/CO Synthesis Gas Composition | |
| F | None | 9.2 |
| G | 0.021 | 15.6 |
| H | 0.03 | 17.3 |
| I | 0.05 | 19.7 |
| J | 0.2 | 28.3 |

[a]Catalysts were tested at 300° C. and a reaction pressure of 2500 psig using a $H_2$/CO synthesis gas composition: Examples A to E were tested at a space velocity of 20,000 $hr^{-1}$ and Examples F to J were tested at 10,000 $hr^{-1}$.
[b]The catalysts consist of 5 weight percent Pd plus the indicated weight percent of Ca supported on Davidson ™ Grade 59 silica gel support.
[c]"Calcium Deposited" refers only to the indicated weight percent of Ca deposited with palladium on the silica gel support and does not include the weight of calcium present in the silica gel.
[d]"Rate" is the rate of synthesis of methanol in pounds of product per cubic foot of catalyst per hour.

TABLE II
METHANOL PRODUCTION DATA[a] FOR PALLADIUM CATALYSTS SUPPORTED ON ALPHA ALUMINA OR MAGNESIUM OXIDE

| EXAMPLE | CATALYST COMPOSITION | SUPPORT | RATE TO METHANOL[b] |
|---|---|---|---|
| K | 5.0% Pd | $\alpha$-$Al_2O_3$ | 1.8 |
| L | 5% Pd + 1% Ca | $\alpha$-$Al_2O_3$ | 6.5 |
| M | 2.5% Pd | MgO | 3.7 |
| N | 2.5% Pd + 0.1% Ca | MgO | 5.2 |

[a]Catalysts were tested at 300° C. and a reaction pressure of 2500 psia using a 1:1 molar ratio of $H_2$:CO synthesis gas composition. Examples K and L were tested at a space velocity of 20,000 $hr^{-1}$ and Examples M and N were tested at 10,000 $hr^{-1}$.
[b]The rate of synthesis of methanol is expressed in pounds of product per cubic foot of catalyst per hour.

What is claimed is:
1. In a heterogeneous process for the production of methanol by the reaction of hydrogen and carbon monoxide in the presence of a palladium-containing catalyst at a temperature of from about 200° C. to about 400° C. and a pressure of from about 150 to about 20,000 psia, the improvement for enhancing the production of methanol which comprises effecting said reaction in the presence of a heterogeneous solid catalyst containing palladium in combination with calcium, the concentration of calcium in the catalyst being at least 0.03 weight percent.

2. The process of claim 1 wherein said catalyst is supported on silica gel.

3. The process of claim 1 wherein the palladium concentration on the catalyst support is from about 2-5% by weight, of the catalyst support.

4. The process of claim 3 wherein the calcium concentration in the catalyst is from about 0.05% to about 1.0% by weight of the catalyst support.

5. The process of claim 1 wherein the reaction temperature is from about 250° C. to about 350° C. and the reaction pressure is from about 150 psia to about 3000 psia.

6. The process of claim 1 wherein said gaseous mixture contains hydrogen and carbon monoxide in a volume ratio of from about 1:5 to about 5:1.

* * * * *